US012684494B2

(12) United States Patent  
Paul et al.

(10) Patent No.: US 12,684,494 B2  
(45) Date of Patent: Jul. 14, 2026

(54) VARIABLE POWER TRANSMISSION FOR BATTERY-POWERED DEVICES

(71) Applicant: Dexcom, Inc., San Diego, CA (US)

(72) Inventors: Nathanael Richard Paul, Adams, TN (US); Jorge R. Barreras, Dania Beach, FL (US)

(73) Assignee: Dexcom, Inc., San Diego, CA (US)

( * ) Notice: Subject to any disclaimer, the term of this patent is extended or adjusted under 35 U.S.C. 154(b) by 313 days.

(21) Appl. No.: 18/485,969

(22) Filed: Oct. 12, 2023

(65) Prior Publication Data

US 2024/0196336 A1    Jun. 13, 2024

Related U.S. Application Data

(60) Provisional application No. 63/387,058, filed on Dec. 12, 2022.

(51) Int. Cl.
| | |
|---|---|
| *H04W 52/24* | (2009.01) |
| *A61B 5/00* | (2006.01) |
| *A61B 5/145* | (2006.01) |
| *H04W 52/36* | (2009.01) |

(52) U.S. Cl.
CPC ......... *H04W 52/241* (2013.01); *A61B 5/0004* (2013.01); *A61B 5/14546* (2013.01); *A61B 5/742* (2013.01); *H04W 52/36* (2013.01)

(58) Field of Classification Search
CPC .... H04W 52/241; H04W 52/36; A61B 5/002; A61B 5/0004; A61B 5/14546; A61B 5/742; A61B 2560/0209; A61B 2560/0204; A61B 2560/0214; A61M 2205/3584
See application file for complete search history.

(56) References Cited

U.S. PATENT DOCUMENTS

| | | | |
|---|---|---|---|
| 2013/0225095 A1* | 8/2013 | Hong | H04B 15/00 455/73 |
| 2017/0258987 A1* | 9/2017 | Caspers | G06F 1/1613 |
| 2019/0307376 A1* | 10/2019 | Hernandez-Rosas | A61B 5/6802 |
| 2020/0178860 A1 | 6/2020 | Masciotti et al. | |
| 2021/0178063 A1* | 6/2021 | Parikh | A61B 5/681 |

FOREIGN PATENT DOCUMENTS

CN        114947834 A      8/2022

OTHER PUBLICATIONS

International Search Report and Written Opinion for Application No. PCT/US2023/076729, mailed Feb. 9, 2024, 14 pages.

* cited by examiner

*Primary Examiner* — Lester G Kincaid

(74) *Attorney, Agent, or Firm* — Klarquist Sparkman, LLP

(57) ABSTRACT

Systems, techniques, and devices for performing variable power transmission for a battery-powered device are disclosed. In certain embodiments, the techniques include determining a proximity of the transmitter to a first display device. An output transmission power of the transmitter is determined based on the proximity. Analyte information from an analyte sensor coupled to the transmitter is transmitted to the first display device at the output transmission power.

29 Claims, 6 Drawing Sheets

400

ENTER

DETERMINE PROXIMITY BETWEEN ANALYTE SENSOR SYSTEM AND A DISPLAY DEVICE — 405

DETERMINE AN OUTPUT TRANSMISSION POWER OF AN ANALYTE SENSOR SYSTEM, BASED ON THE PROXIMITY — 410

TRANSMIT ANALYTE INFORMATION TO THE DISPLAY DEVICE AT THE OUTPUT TRANSMISSION POWER — 415

EXIT

VARIABLE POWER TRANSMISSION FOR BATTERY-POWERED DEVICES

CROSS-REFERENCE TO RELATED APPLICATIONS

This application claims the benefit of U.S. Application Ser. No. 63/387,058 filed on Dec. 12, 2022, and hereby incorporated by reference in its entirety for all purposes.

BACKGROUND

Diabetes is a metabolic condition relating to the production or use of insulin by the body. Insulin is a hormone that allows the body to use glucose for energy, or store glucose as fat.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic patient carries a self-monitoring blood glucose (SMBG) monitor, which may require uncomfortable finger pricking methods. Due to the lack of comfort and convenience, a diabetic will normally only measure his or her glucose level two to four times per day. Unfortunately, these time intervals are spread so far apart that the diabetic will likely be alerted to a hyperglycemic or hypoglycemic condition too late, sometimes incurring dangerous side effects as a result. In fact, it is unlikely that a diabetic will take a timely SMBG value, and further the diabetic will not know if his blood glucose value is going up (higher) or down (lower), due to limitations of conventional methods.

Consequently, a variety of non-invasive, transdermal (e.g., transcutaneous) and/or implantable sensors are being developed for continuously detecting and/or quantifying blood glucose values. Generally, in a diabetes management system, a transmitter associated with the sensor wirelessly transmits raw or minimally processed data for subsequent display and/or analysis at one or more display devices, which can include a mobile device, a server, or any other type of communication devices. A display device, such as a mobile device, may then utilize a trusted software application (e.g., approved and/or provided by the manufacturer of the sensor), which takes the raw or minimally processed data and provides the user with information about the user's blood glucose levels. Because diabetes management systems using such implantable sensors can provide more up-to-date information to users, they may reduce the risk of a user failing to regulate the user's blood glucose levels.

This background is provided to introduce a brief context for the summary and detailed description that follow. This background is not intended to be an aid in determining the scope of the claimed subject matter nor be viewed as limiting the claimed subject matter to implementations that solve any or all of the disadvantages or problems presented above.

SUMMARY

Certain embodiments provide a computer-implemented method for performing variable power transmission of a transmitter of an analyte sensor system. The computer-implemented method includes determining a proximity of the transmitter to a first display device. The computer-implemented method also includes determining an output transmission power of the transmitter based on the proximity. The computer-implemented method further includes transmitting analyte information from an analyte sensor coupled to the transmitter to the first display device at the output transmission.

Certain embodiments provide an analyte sensor system. The analyte sensor system includes an analyte sensor system and sensor electronics. The sensor electronics are coupled to the analyte sensor system and include a processor and a transmitter. The processor is configured to determine a proximity of the transmitter to a first display device. The processor is also configured to determine an output transmission power of the transmitter based on the proximity. The transmitter is configured to transmit analyte information from the analyte sensor to the first display device at the output transmission power.

Certain embodiments provide a non-transitory computer-readable medium. The non-transitory computer-readable medium stores computer-executable instructions, which when executed by one or more processors of a display device, performs an operation for variable power transmission of a transmitter of an analyte senor system. The operation includes determining a proximity of the transmitter to a display device. The operation also includes determining an output transmission power of the transmitter based on the proximity. The operation further includes transmitting analyte information from an analyte sensor coupled to the transmitter to the display device at the output transmission power.

Certain embodiments provide a display device. The display device includes one or more memories collectively storing computer-executable instructions. The display device also includes one or more processors coupled to the one or more memories. The one or more processors are collectively configured to execute the computer-executable instructions and cause the display device to perform an operation. The operation includes determining a pattern of proximity of the display device to a transmitter of an analyte sensor system. The operation also includes transmitting an indication of the pattern of proximity to the analyte sensor system. The operation further includes receiving an analyte transmission from the transmitter, the analyte transmission having an output transmission power based at least in part on the indication.

Certain embodiments provide a system. The system includes a display device and an analyte sensor system. The analyte sensor system includes an analyte sensor and a transmitter. The analyte sensor system is configured to determine a proximity of the transmitter to the display device, determine an output transmission power of the transmitter based on the proximity, and transmit, via the transmitter, analyte information from the analyte sensor to the display device at the output transmission power.

DETAILED DESCRIPTION OF CERTAIN INVENTIVE EMBODIMENTS

Figure 1A:
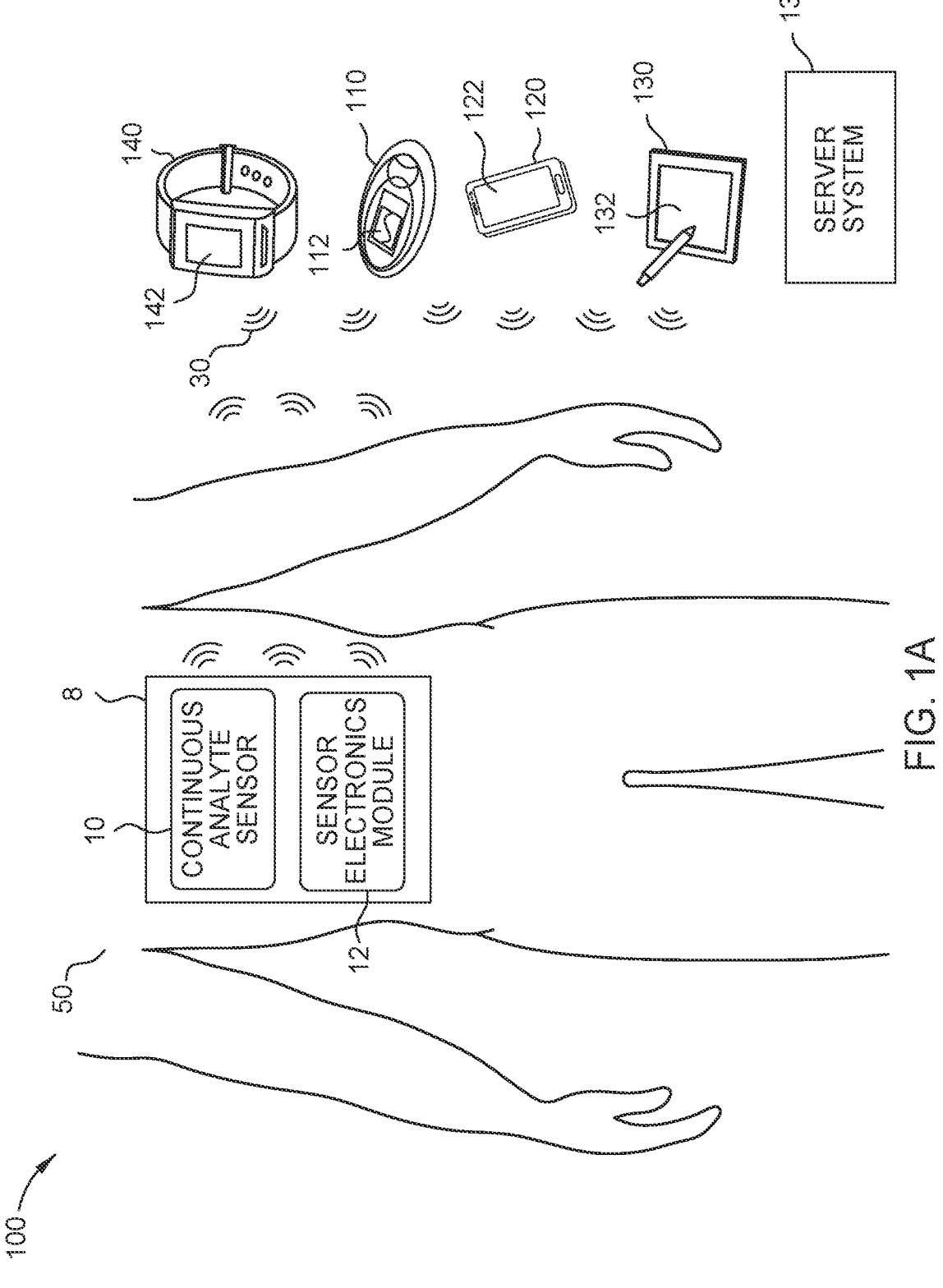
FIG. 1A illustrates an example disease management system, according to certain embodiments disclosed herein.

Many medical device systems may use battery-powered devices to transmit health-related data. For example, in a continuous glucose monitor (CGM) system, a glucose sensor may measure glucose levels of a patient and communicate the raw sensor measurements to a battery-powered transmitter, which may then transmit corresponding glucose values to a patient's display device, such as a mobile phone.

The battery-powered devices in many medical device systems generally transmit at a near-constant transmission power to communicate data. For example, in a CGM system, a patient's battery-powered transmitter (hereinafter, "transmitter") may exchange wireless data with a display device (e.g., phone and/or dedicated display device) at a near-constant transmission power to allow a message to reach a recipient that may be a large distance away from the transmitter, to overcome potential signal losses that can prevent the message from being received by a recipient, etc. For instance, the transmitter may use a near-constant maximum power to transmit messages to the display device regardless of how close the display device is to the transmitter or whether the distance between the display device and the transmitter changes. In another example, in situations where the patient's transmitter is connected with a primary display device, the patient's transmitter may similarly transmit messages at near-constant transmission power regardless of whether a secondary display device (that can communicate with both the transmitter and the primary display device) is or becomes available that is closer to the transmitter than the primary display device.

Although transmitting messages at a near-constant transmission power may allow a message to reach a recipient that may be a large distance away from the transmitter, for battery-powered medical devices, transmitting messages at such a near-constant transmission power can lead to unnecessary battery consumption and significantly reduce the battery life of the medical devices. Accordingly, there is a need for improvements to techniques for transmitting data (e.g., a patient's glucose data) by battery-powered transmitter(s).

Accordingly, certain embodiments described herein relate to a number of techniques for reducing or optimizing battery consumption of a battery-powered transmitter by reducing or optimizing the amount of power that the transmitter uses to transmit messages over time. The transmission power reduction or optimization described herein may be implemented when certain conditions are satisfied.

In one exemplary embodiment, the condition is based on a proximity of the transmitter to one or more display devices. In certain scenarios, for example, the patient may be engaging in an activity (e.g., sleeping, driving, exercising, etc.) during certain times where the patient's transmitter is in close proximity to the patient's display device (e.g., phone, smartwatch, etc.). In some other scenarios, the patient's transmitter may be in closer proximity to a secondary display device (e.g., another user's display device) than a primary display device (e.g., the patient's display device). The proximity of the transmitter to a display device (s) may be inferred (or detected) based on one or more of (or a combination of) sensor data obtained from sensor(s) (e.g., accelerometer, global positioning system (GPS), gyroscope, optical sensor, etc.) of the display device, a signal strength of the display device, a location of the transmitter, etc. When proximity of the transmitter to a display device(s) is less than a threshold distance, the transmitter may reduce the transmission power.

Advantageously, performing variable power transmission using the techniques described herein reduces battery consumption, which is critical to extending the operational life of the transmitter. The techniques described herein for performing variable power transmission of a transmitter are described more fully herein with respect to FIGS. 1A-1B and 2-5 below. Note that, hereinafter, although certain embodiments described herein refer to an analyte sensor system performing one or more techniques described herein for variable power transmission, it is the transmitter (also referred to as the sensor electronics module) in the analyte sensor system that performs the techniques described herein for variable power transmission and communication with a display device. Additionally, note that although certain embodiments herein are described with respect to the management of diabetes, a glucose sensor system, and the transmission of glucose measurement between the devices, the protocols and techniques described herein are similarly applicable to any type of health management system that includes any type of analyte sensor (e.g., lactate sensor, ketone sensor, etc.).

Example Analyte Sensor System

FIG. 1A depicts a disease management system 100 ("system 100"), such as a diabetes management system, that may be used in connection with certain embodiments of the present disclosure. Certain such embodiments may involve performing variable power transmission over time to reduce battery consumption by the transmitter. For example, the variable power transmission may include reducing transmission power of the transmitter when the transmitter is in close proximity to a display device(s) and/or increasing transmission power of the transmitter when the transmitter is not in close proximity to the display device(s). System 100 depicts aspects of analyte sensor system 8 (hereinafter "SS 8") that may be communicatively coupled to display devices 110, 120, 130, and 140 and/or server system 134.

In certain embodiments, SS 8 is provided for measurement of an analyte in a host or a user. By way of an overview and an example, SS 8 may be implemented as an encapsulated microcontroller that makes sensor measurements, generates analyte data (e.g., by calculating values for continuous glucose monitoring data), and engages in wireless communications (e.g., via Bluetooth and/or other wireless protocols) to send such data to remote devices, such as display devices 110, 120, 130, 140 and/or server system 134. Paragraphs [0137]-[0140] and FIGS. 3A, 3B, and 4 of U.S. App. No. 2019/0336053 further describe an on-skin sensor assembly that, in certain embodiments, may be used in connection with SS 8. Paragraphs [0137]-[0140] and FIGS. 3A, 3B, and 4 of U.S. App. No. 2019/0336053 are incorporated herein by reference.

In certain embodiments, SS 8 includes an analyte sensor electronics module 12 and an analyte sensor 10 associated with analyte sensor electronics module 12. In certain embodiments, analyte sensor electronics module 12 includes electronic circuitry associated with measuring and processing analyte sensor data or information, including algorithms associated with processing and/or calibration of the analyte sensor data/information. Analyte sensor electronics module 12 may be physically/mechanically connected to analyte sensor 10 and can be integral with (i.e., non-releasably attached to) or releasably attachable to analyte sensor 10.

Analyte sensor electronics module 12 may also be electrically coupled to analyte sensor 10, such that the components may be electromechanically coupled to one another (e.g., (a) prior to insertion into a patient's body, or (b) during the insertion into the patient's body). Analyte sensor electronics module 12 may include hardware, firmware, and/or software that enable measurement and/or estimation of levels of the analyte in a host/user via analyte sensor 10 (e.g., which may be/include a glucose sensor). For example, analyte sensor electronics module 12 can include one or more potentiostats, a power source for providing power to analyte sensor 10, other components useful for signal processing and data storage, and a telemetry module for transmitting data from the sensor electronics module to one or more display devices. Electronics can be affixed to a printed circuit board (PCB) within SS 8, or platform or the like, and can take a variety of forms. For example, the electronics can take the form of an integrated circuit (IC), such as an Application-Specific Integrated Circuit (ASIC), a microcontroller, a processor, and/or a state machine.

Analyte sensor electronics module 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

Analyte sensor 10 is configured to measure a concentration or level of the analyte in the host. The term analyte is further defined by paragraph of U.S. App. No. 2019/0336053. Paragraph of U.S. App. No. 2019/0336053 is incorporated herein by reference. In some embodiments, analyte sensor 10 includes a continuous glucose sensor, such as a subcutaneous, transdermal (e.g., transcutaneous), or intravascular device. In some embodiments, analyte sensor 10 can analyze a plurality of intermittent blood samples. Analyte sensor 10 can use any method of glucose-measurement, including enzymatic, chemical, physical, electrochemical, spectrophotometric, polarimetric, calorimetric, iontophoretic, radiometric, immunochemical, and the like. Additional details relating to a continuous glucose sensor are provided in paragraphs-[0076] of U.S. application Ser. No. 13/827,577. Paragraphs [0072]-[0076] of U.S. application Ser. No. 13/827,577 are incorporated herein by reference. In certain embodiments, analyte sensor 10 may be configured to sense multiple analytes (e.g., glucose, potassium, lactate, and/or others).

With further reference to FIG. 1A, display devices 110, 120, 130, and/or 140 can be configured for displaying (and/or alarming) displayable sensor information that may be transmitted by sensor electronics module 12 (e.g., in a customized data package that is transmitted to the display devices based on their respective preferences). Each of display devices 110, 120, 130, or 140 may respectively include a display such as touchscreen display 112, 122, 132, and/or 142 for displaying sensor information and/or analyte data to a user and/or receiving inputs from the user. For example, a graphical user interface (GUI) may be presented to the user for such purposes. In certain embodiments, the display devices may include other types of user interfaces such as voice user interface instead of or in addition to a touchscreen display for communicating sensor information to the user of the display device and/or receiving user inputs. In certain embodiments, one, some, or all of display devices 110, 120, 130, 140 may be configured to display or otherwise communicate the sensor information as it is communicated from sensor electronics module 12 (e.g., in a data package that is transmitted to respective display devices), without any additional prospective processing required for calibration and/or real-time display of the sensor data.

The plurality of display devices 110, 120, 130, 140 depicted in FIG. 1A may include a custom or proprietary display device, for example, analyte display device, especially designed for displaying certain types of displayable sensor information associated with analyte data received from sensor electronics module 12 (e.g., a numerical value and/or an arrow, in certain embodiments). In certain embodiments, one of the plurality of display devices 110, 120, 130, 140 includes a smartphone, such as display device 120, based on an Android, iPhone Operating System (iOS), or another operating system configured to display a graphical representation of the continuous sensor data (e.g., including current and/or historic data). In certain embodiments, system 100 further includes a medical delivery device (e.g., an insulin pump or pen). Sensor electronics module 12 may be configured to transmit sensor information and/or analyte data to the medical delivery device. The medical delivery device (not shown) may be configured to administer a certain dosage of insulin or another medicament to the user based on the sensor information and/or analyte data (e.g., which may include a recommended insulin dosage) received from the sensor electronics module 12.

Server system 134 may be used to directly or indirectly collect analyte data from SS 8 and/or the plurality of display devices, for example, to perform analytics thereon, generate universal or individualized models for analyte levels and profiles, provide services or feedback (including from individuals or systems remotely monitoring the analyte data), perform or assist SS 8 and display device 150 with identification, authentication, etc., according to the embodiments described herein. Note that, in certain embodiments, server system 134 may be representative of multiple systems or computing devices that perform the functions of server system 134 (e.g., in a distributed manner).

Figure 1B:
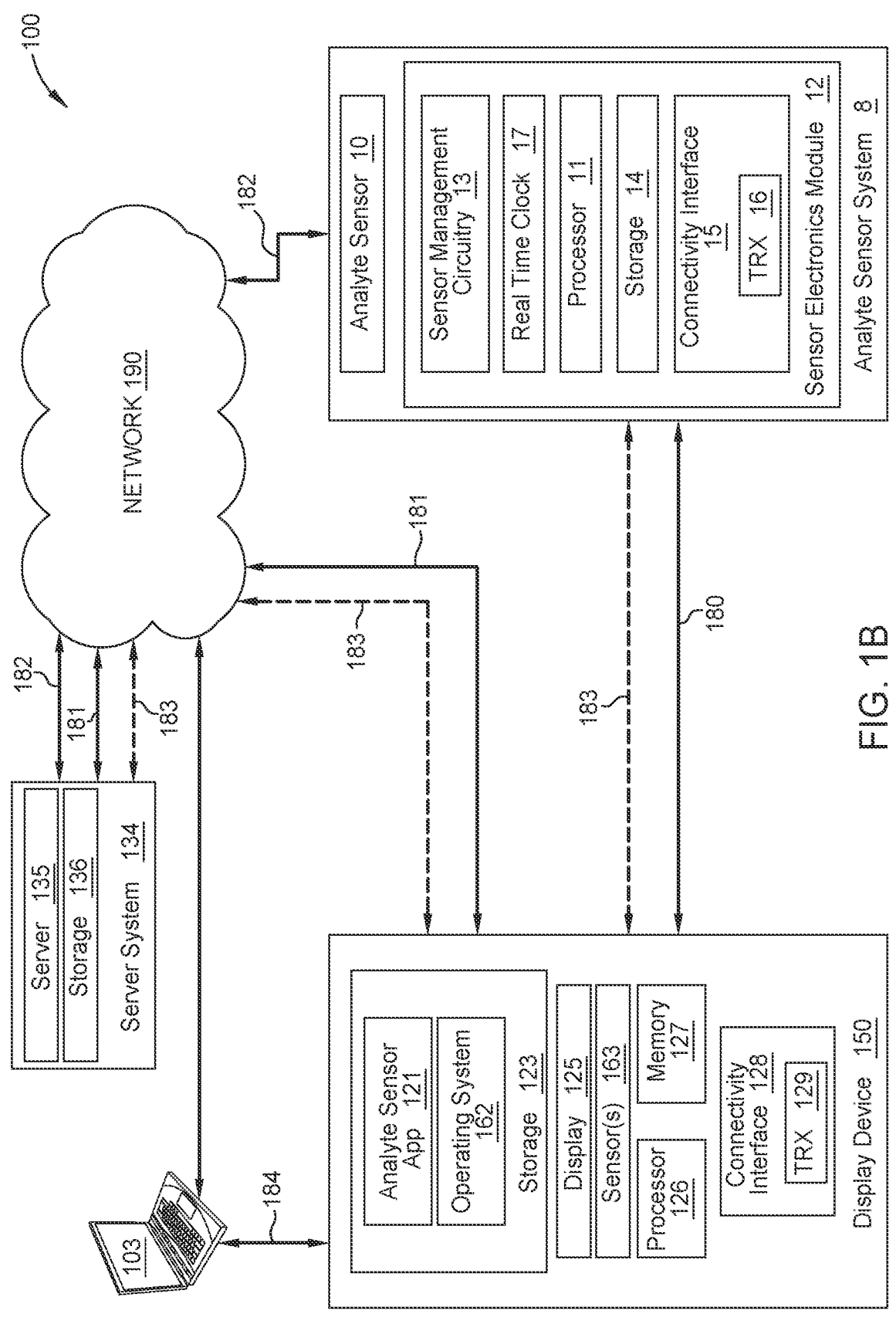
FIG. 1B illustrates the example disease management system of FIG. 1A in more detail, according to certain embodiments disclosed herein.

FIG. 1B illustrates a more detailed view of system 100 including a display device 150 that is communicatively coupled to SS 8. In certain embodiments, display device 150 may be any one of display devices 110, 120, 130, and 140 of FIG. 1A. The communication path between SS 8 and display device 150 is shown as communication path 180. In certain embodiments, SS 8 and display device 150 are configured to wirelessly communicate over communication path 180 using low range and/or distance wireless communication protocols. Examples of low range and/or distance wireless communication protocols include Bluetooth and Bluetooth Low Energy (BLE) protocols. In certain embodiments, other short range wireless communications may include Near Field Communications (NFC), radio frequency identification (RFID) communications, IR (infra red) communications, and optical communications, as illustrative, non-limiting examples. In certain embodiments, wireless communication protocols other than low range and/or distance wireless communication protocols may be used for communication path 180, such as WiFi Direct. Display device 150 is also configured to connect to network 190 (e.g., local area network (LAN), wide area network (WAN), the Internet, etc.). For example, display device 150 may connect to network 190 via a wired (e.g., Ethernet) or wireless (e.g., wireless LAN (WLAN), wireless WAN, cellular, Mesh network, personal area network (PAN) etc.) interface. Display device 150 is able to communicate with server system 134 through network 190. The communication path between display device 150 and server system 134 is shown as communication path 181 via network 190.

Note that, in certain embodiments, SS 8 may be able to independently (e.g., wirelessly) communicate with server system 134 through network 190. An independent communication path between SS 8 and server system 134 is shown as communication path 182. However, in certain other embodiments, SS 8 may not be configured with the necessary hardware/software to establish, for example, an independent wireless communication path with server system 134 through network 190. In such embodiments, SS 8 may communicate with server system 134 through display device 150. An indirect or pass-through communication path between SS 8 and server system 134 is shown as communication path 183.

In embodiments where display device 150 is a proprietary display device, such as display device 110 designed specifically for the communication of analyte data, display device 150 may not be configured with the necessary hardware/software for independently connecting to network 190. Instead, in certain such embodiments, display device 150 is configured to establish a wired or wireless communication path 184 (e.g., through a Universal System Bus (USB) connection) with computer device 103, which is configured to communicate with server system 134 through network 190. For example, computer device 103 may connect to network 190 via a wired (e.g., Ethernet) or wireless (e.g., WLAN, wireless WAN, cellular, etc.) interface. Note that in the embodiments described in relation to FIGS. 2-5, unless otherwise noted, display device 150 is assumed to be capable of independently communicating with server system 134 through network 190, independent of computer device 103.

System 100 additionally includes server system 134, which in turn includes server 135 that is coupled to storage 136 (e.g., one or more computer storage systems, cloud-based storage systems and/or services, etc.). In certain embodiments, server system 134 may be located or execute in a public or private cloud. In certain embodiments, server system 134 is located or executes on-premises ("on-prem"). As discussed, server system 134 is configured to receive, collect, and/or monitor information, including analyte data and related information, as well as encryption/authentication information from SS 8 and/or display device 150. Such information may include input responsive to the analyte data or input (e.g., the user's glucose measurements and other physiological/behavioral information) received in connection with an analyte monitoring or sensor application running on SS 8 or display device 150. This information may be stored in storage 136 and may be processed, such as by an analytics engine capable of performing analytics on the information. An example of an analyte sensor application that may be executable on display device 150 is analyte sensor application 121, further described below.

In certain embodiments, server system 134 at least partially directs communications between SS 8 and display device 150, for example, for facilitating authentication therebetween. Such communications include messaging (e.g., advertisement, command, or other messaging), message delivery, and analyte data. For example, in certain embodiments, server system 134 may process and exchange messages between SS 8 and display device 150 related to frequency bands, timing of transmissions, security, alarms, and so on. In certain embodiments, server system 134 may also update information stored on SS 8 and/or display device 150. In certain embodiments, server system 134 may send/receive information to/from SS 8 and or display device 150 in real-time or sporadically. Further, in certain embodiments, server system 134 may implement cloud computing capabilities for SS 8 and/or display device 150.

FIG. 1B also illustrates the components of SS 8 in further detail. As shown, in certain embodiments, SS 8 includes analyte sensor 10 coupled to sensor electronics module 12. Sensor electronics module 12 includes sensor measurement circuitry (SMC) 13 that is coupled to analyte sensor 10 for processing and managing sensor data. SMC 13 may also be coupled to processor 11. In some embodiments, processor 11 may perform part or all of the functions of the SMC 13 for obtaining and processing sensor measurement values from analyte sensor 10. Processor 11 may also be coupled to storage 14 and real time clock (RTC) 17 for storing and tracking sensor data. In addition, processor 11 may be further coupled to a connectivity interface 15, which includes a radio unit or transceiver (TRX) 16 for sending sensor data and receiving requests and commands from an external device, such as display device 150. As used herein, the term transceiver generally refers to a device or a collection of devices that enable SS 8 to (e.g., wirelessly) transmit and receive data. SS 8 may further include storage 14 and real time clock (RTC) 17 for storing and tracking sensor data. It is contemplated that, in some embodiments, the SMC 13 may carry out all the functions of the processor 11 and vice versa.

Transceiver 16 may be configured with the necessary hardware and wireless communications protocols for enabling wireless communications between SS 8 and other devices, such as display device 150 and/or server system 134. For example, as described above, transceiver 16 may be configured with the necessary hardware and communication protocols to establish a Bluetooth or BLE connection with display device 150. As one of ordinary skill in the art appreciates, in such an example, the necessary hardware may include a Bluetooth or BLE security manager and/or other Bluetooth or BLE related hardware/software modules configured for Bluetooth or BLE communications standards. In some embodiments where SS 8 is configured to establish an independent communication path with server system 134, transceiver 16 may be configured with the necessary hardware and communication protocols (e.g., long range wireless cellular communication protocol, such as, Global System for Mobile Communications (GSM), Code-Division Multiple Access (CDMA), Long-Term Evolution (LTE), Voice over LTE (VOLTE), 3G, 4G, and 5G communication protocols, WiFi communication protocols, such as 802.11 communication protocols, etc.) for establishing a wireless connection to network 190 to connect with server system

134. As discussed elsewhere, other short range protocols, may also be used for communication between display device 150 and a SS 8 such as NFC, RFID, etc.

FIG. 1B similarly illustrates the components of display device 150 in further detail. As shown, display device 150 includes connectivity interface 128, processor 126, memory 127, one or more sensors 163, a display 125 for presenting a graphical user interface (GUI), and a storage 123. A bus (not shown here) may be used to interconnect the various elements of display device 150 and transfer data between these elements. Connectivity interface 128 includes a transceiver (TRX) 129 used for receiving sensor data from SS 8 and for sending requests, instructions, and/or data to SS 8 as well as server system 134. Transceiver 129 is coupled to other elements of display device 150 via connectivity interface 128 and/or the bus. Transceiver 129 may include multiple transceiver modules operable on different wireless standards. For example, transceiver 129 may be configured with one or more communication protocols, such as wireless communication protocol(s) for establishing a wireless communication path with network 190 and/or low range wireless communication protocol(s) (e.g., Bluetooth or BLE) for establishing a wireless communication path 180 with SS 8. Additionally, connectivity interface 128 may in some cases include additional components for controlling radio and/or wired connections, such as baseband and/or Ethernet modems, audio/video codecs, and so on. Sensor(s) 163 may include, but is not limited to, accelerometer(s), gyroscope(s), global positioning system (GPS) sensor(s), heart rate sensor (s), optical sensor(s), etc. Note that while sensor(s) 163 are shown integral to the display device, in certain embodiments, one or more of sensor(s) 163 may be standalone sensors (e.g., separate from the display device 150).

In some embodiments, when a standardized communication protocol is used between display device 150 and SS 8, commercially available transceiver circuits may be utilized that incorporate processing circuitry to handle low level data communication functions such as the management of data encoding, transmission frequencies, handshake protocols, security, and the like. In such embodiments, processor 126 of display device 150 and/or processor 11 of SS 8 may not need to manage these activities, but instead provide desired data values for transmission, and manage high level functions such as power up or power down, set a rate at which messages are transmitted, and the like. Instructions and data values for performing these high level functions can be provided to the transceiver circuits via a data bus and transfer protocol established by the manufacturer of transceivers 129 and 16. However, in embodiments where a standardized communication protocol is not used between transceivers 129 and 16 (e.g., when non-standardized or modified protocols are used), processors 126 and 11 may be configured to execute instructions associated with proprietary communications protocols (e.g., one or more of the communications protocols described herein) to control and manage their respective transceivers. In addition, when non-standardized or modified protocols are used, customized circuitries may be used to service such protocols.

Processor 126 may include processor sub-modules, including, by way of example, an applications processor that interfaces with and/or controls other elements of display device 150 (e.g., connectivity interface 128, analyte sensor application 121 (hereinafter "sensor application 121"), display 125, sensor(s) 163, memory 127, storage 123, etc.). In certain embodiments, processor 126 is configured to perform functions related to device management, such as, managing lists of available or previously paired devices, information related to network conditions (e.g., link quality and the like), information related to the timing, type, and/or structure of messaging exchanged between SS 8 and display device 150, as illustrative, non-limiting examples. Processor 126 may further be configured to receive and process user input, such as, for example, a user's biometric information, such as the user's finger print (e.g., to authorize the user's access to data or to be used for authorization/encryption of data, including analyte data), as well as analyte data.

Processor 126 may include and/or be coupled to circuitry such as logic circuits, memory, a battery and power circuitry, and other circuitry drivers for periphery components and audio components. Processor 126 and any sub-processors thereof may include logic circuits for receiving, processing, and/or storing data received and/or input to display device 150, and data to be transmitted or delivered by display device 150. As described above, processor 126 may be coupled by a bus to display 125, connectivity interface 128, storage 123, etc. Hence, processor 126 may receive and process electrical signals generated by these respective elements and thus perform various functions. By way of example, processor 126 may access stored content from storage 123 and memory 127 at the direction of analyte sensor application 121, and process the stored content to be displayed by display 125. Additionally, processor 126 may process the stored content for transmission via connectivity interface 128 to SS 8 and/or server system 134. Display device 150 may include other peripheral components not shown in detail in FIG. 1B.

In certain embodiments, memory 127 may include volatile memory, such as random access memory (RAM) for storing data and/or instructions for software programs and applications, such as analyte sensor application 121. Display 125 presents a GUI associated with operating system 162 and/or analyte sensor application 121. In various embodiments, a user may interact with analyte sensor application 121 via a corresponding GUI presented on display 125. By way of example, display 125 may be a touchscreen display that accepts touch input. Analyte sensor application 121 may process and/or present analyte-related data received by display device 150 and present such data via display 125. Additionally, analyte sensor application 121 may be used to obtain, access, display, control, and/or interface with analyte data and related messaging and processes associated with SS 8 (e.g., and/or any other medical device (e.g., insulin pump or pen) that are communicatively coupled with display device 150), as is described in further detail herein.

Storage 123 may be a non-volatile storage for storing software programs, instructions, data, etc. For example, storage 123 may store analyte sensor application 121 that, when executed using processor 126, for example, receives input (e.g., by a conventional hard/soft key or a touch screen, voice detection, or other input mechanism), and allows a user to interact with the analyte data and related content via display 125. In various embodiments, storage 123 may also store user input data and/or other data collected by display device 150 (e.g., input from other users gathered via analyte sensor application 121). Storage 123 may further be used to store volumes of analyte data received from SS 8 (or any other medical data received from other medical devices (e.g., insulin pump, pen, etc.) for later retrieval and use, e.g., for determining trends and triggering alerts.

As described above, SS 8, in certain embodiments, gathers analyte data from analyte sensor 10 and transmits the same or a modified version of the collected data to display device 150. Data points regarding analyte values may be gathered and transmitted over the life of analyte sensor 10

(e.g., in the range of 1 to 30 days or more). New measurements may be transmitted often enough to adequately monitor glucose levels. In certain embodiments, rather than having the transmission and receiving circuitry of each of SS 8 and display device 150 continuously communicate, SS 8 and display device 150 may regularly and/or periodically establish a communication channel among each other. Thus, in such embodiments, SS 8 may, for example, communicate with display device 150 at predetermined time intervals. The duration of the predetermined time interval can be selected to be long enough so that SS 8 does not consume too much power by transmitting data more frequently than needed, yet frequent enough to provide substantially real-time sensor information (e.g., measured glucose values or analyte data) to display device 150 for output (e.g., via display 125) to the user. While the predetermined time interval is every five minutes in some embodiments, it is appreciated that this time interval can be varied to be any desired length of time. In other embodiments, transceivers 129 and 16 may be continuously communicating. For example, in certain embodiments, transceivers 129 and 16 may establish a session or connection there between and continue to communicate together until the connection is lost.

Analyte sensor application 121 may be downloaded, installed, and initially configured/setup on display device 150. For example, display device 150 may obtain analyte sensor application 121 from server system 134, or from another source, such as an application store or the like, via a network, e.g., network 190. Following installation and setup, analyte sensor application 121 may be configured to access, process, and/or interface with analyte data (e.g., whether stored on server system 134, locally from storage 123, from SS 8, or any other medical device). By way of example, analyte sensor application 121 may present a menu that includes various controls or commands that may be executed in connection with the operation of SS 8, display device 150, one or more other display devices (e.g., display device 110, 130, 140, etc.), and/or one or more other partner devices, such as an insulin pump. For example, analyte sensor application 121 may be used to interface with or control other display and/or partner devices, for example, to deliver or make available thereto analyte data, including for example by receiving/sending analyte data directly to the other display and/or partner device and/or by sending an instruction for SS 8 and the other display and/or partner device to be connected.

After downloading analyte sensor application 121, as one of the initial steps, the user may be directed by analyte sensor application 121 to wirelessly connect display device 150 to the user's SS 8, which the user may have already placed on their body. A wireless communication path 180 between display device 150 and SS 8 allows SS 8 to transmit analyte measurements to display device 150 and for the two devices to engage in any of the other interactions described herein.

Example Variable Power Transmission for Battery-Powered Devices

As discussed, the SS 8 may transmit at a near-constant transmission power to communicate data. The SS 8 may use a near-constant transmission power to allow a message to reach a recipient that may be large distance away from the SS 8, overcome potential signal losses that can prevent the message from being received by a recipient, etc. As noted, however, one issue with using a near-constant transmission power to transmit messages is that the SS 8 is generally configured to use the near-constant transmission power regardless of how close the SS 8 is to a display device 150 or whether the distance between the display device 150 and the SS 8 changes. Using such a constant transmission power to transmit messages at all times can lead to unnecessary battery consumption, which can reduce the operational life of the SS 8.

For instance, during certain times, the patient may be engaging in an activity in which the patient's SS 8 is in close proximity to the patient's display device 150. Examples of such activities include, but are not limited to, sleeping, driving, exercising, eating, etc. Additionally or alternatively, there may be scenarios in which the patient's SS 8 is in closer proximity to a secondary display device than a primary display device, such as the patient's display device. The secondary display device may be a display device of another user (e.g., family member or friend) that is associated with the patient. Such a secondary display device may be configured to receive analyte data from the patient's SS 8 and/or patient's display device 150. In scenarios where the patient's display device 150 is in close proximity to the patient's SS 8, using a near-constant transmission power (e.g., a maximum transmission power) to transmit messages is unnecessary as a lower transmission power may be sufficient to allow a message to reach a recipient in close proximity to the patient's SS 8. Consequently, using a near-constant transmission power in these scenarios may cause unnecessary battery consumption, reducing the operational life of the SS 8.

To address the issues associated with using a near-constant transmission power for transmission of messages, certain embodiments described herein provide techniques for varying (e.g., reducing) the amount of power that the patient's SS 8 uses to transmit messages over time. The variable power transmission described herein may include performing transmission power reduction when a certain condition(s) is satisfied. In an exemplary embodiment, the condition(s) is based on a proximity of the patient's SS 8 to one or more display devices 150. For example, when the patient is engaging in an activity, such as sleeping, driving, exercising, eating, etc., the patient's SS 8 may be in close proximity to the patient's display device 150, thereby making it technically advantageous for the patient's SS 8 to use a lower transmission power to transmit messages to the patient's display device 150. In some examples, the close proximity may include a predefined distance, a predetermined signal strength or power threshold. Additionally or alternatively, in certain scenarios, the patient's SS 8 may be in closer proximity to a secondary display device 150 (e.g., a display device of a family member/friend of the patient) than a primary display device 150 (e.g., patient's display device), thereby making it technically advantageous for the patient's SS 8 to use a lower transmission power to transmit messages to the secondary display device 150 as opposed to using a higher transmission power to transmit messages to the primary display device 150. The proximity of the patient's SS 8 to a display device(s) 150 may be determined by the patient's SS 8 and/or the display device(s) 150. The proximity of the SS 8 to a display device 150 may be inferred (or detected) based on one or more of (or a combination of) sensor data obtained from sensor(s) 163 of the display device 150, a signal strength of the display device 150, a location of the SS 8, etc.

Figure 2:
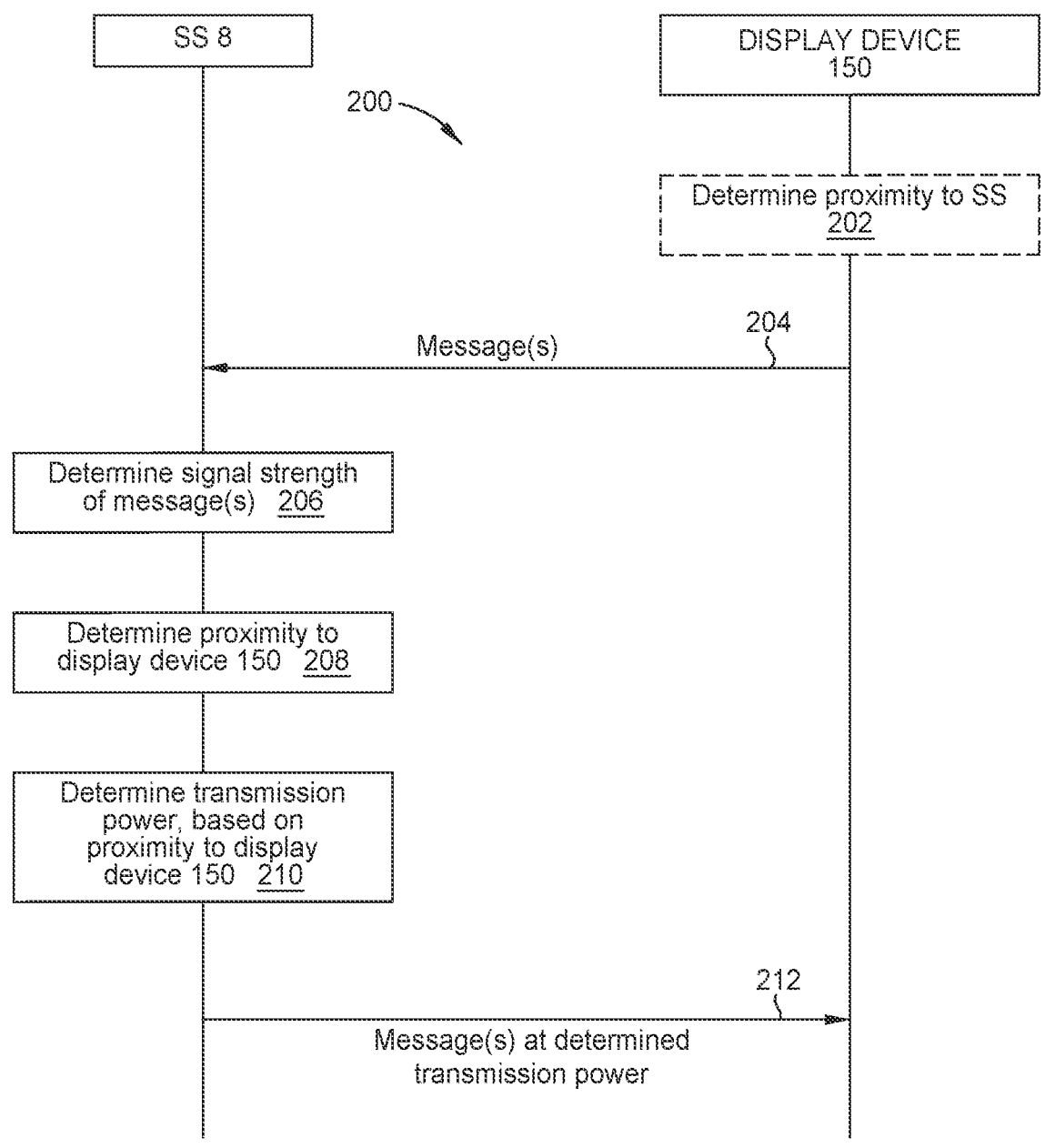
FIG. 2 is a sequence diagram illustrating example operations performed by an analyte sensor system and a display device, according to certain embodiments described herein.

FIG. 2 is a sequence diagram 200 illustrating example operations performed by an SS 8 and a display device 150, according to certain embodiments described herein. Note that certain steps in sequence diagram 200 may occur out of the order noted in FIG. 2. For example, two steps shown in succession may, in fact, be executed substantially concurrently, or the steps may sometimes be executed in the reverse order, depending upon the functionality involved.

At step 208, the SS 8 determines a proximity to the display device 150. In certain embodiments, the SS 8 (at step 208) determines the proximity to the display device 150, based on a signal strength of the display device 150. For example, at step 204, the SS 8 may receive one or more messages from the display device 150 and, at step 206, the SS 8 may determine a signal strength of the message(s) (e.g., a received signal strength indicator (RSSI)). In such an example, the proximity determination in step 208 may be based on the signal strength of the messages.

In certain embodiments, the SS 8 (at step 208) determines the proximity to the display device 150, based on a location of the SS 8 and/or time instance, such as a time of day. As discussed, during certain times of day, the patient's SS 8 and the patient's display device 150 may be in close proximity. For example, the patient's SS 8 and the patient's display device 150 may be in proximity when the patient is eating, sleeping, exercising, commuting to/from work, etc. In such embodiments, when the patient's SS 8 detects that it is in a predefined location and/or a particular time of day has occurred, then the patient's SS 8 may infer that the patient's display device 150 is in close proximity to the patient's SS 8.

In certain embodiments, the patient's SS 8 infers that the patient's SS 8 and the patient's display device 150 are in close proximity during certain times and/or certain locations, based on a user pattern determined by the display device 150 and communicated to the patient's SS 8. The user pattern may indicate a pattern of proximity of the patient's SS 8 and the patient's display device 150 during certain times and/or certain locations.

The patient's display device 150 can implement a learning algorithm to determine the user pattern. For example, the display device 150 may periodically prompt the patient at certain times (e.g., nighttime, lunchtime, while exercising, etc.) over one or more days to confirm that the patient keeps their display device in close proximity to them, and thereby, their SS 8. Based on the patient input, the display device 150 may then determine a pattern associated with the proximity of the display device 150 and the SS 8. An exemplary user pattern may indicate that the patient's display device 150 is always in proximity to the patient's SS 8 in particular locations and/or certain times of day (e.g., nighttime, lunchtime, while exercising, etc.). At such particular locations and/or certain times of day, the patient may be engaging in activities, including, but not limited to, eating, driving, sleeping, exercising, and so on.

The display device 150 may transmit an indication associated with the user pattern to the SS 8. In FIG. 2, for example, such an indication associated with the user pattern may be included in one of the messages transmitted to the patient's SS 8 in step 204. The SS 8 may store the indication of the user pattern, e.g., in storage 14. At step 208, the SS 8 may determine proximity to the display device 150, based on the indication associated with the user pattern.

In certain embodiments, the patient's SS 8 infers that the patient's SS 8 and the patient's display device 150 are in close proximity during certain times based on whether the display device 150 is charging. In such embodiments, the display device 150 (e.g., watch, phone) can self-identify when it is charging. The display device 150 may also determine other information during the charging status, including, for example, whether the display device 150 is on a home network, the associated time of day, RSSI of the patient's SS 8, etc. The display device 150 can use this information (e.g., charging status, time of day, RSSI, network, etc.) to infer that the display device 150 is in close proximity to the patient's SS 8. The display device 150 may communicate the proximity determination in one of the messages transmitted to the patient's SS 8 in step 204. Alternatively, in some embodiments, the SS 8 may directly send messages in step 212 to display device 150 in a determined transmission power based solely on the status of the display device (e.g., charging status) without directly inferring the proximity from the SS 8.

In certain embodiments, the patient's SS 8 infers that the patient's SS 8 and the patient's display device 150 are in close proximity during certain times based on a user pattern determined by the patient's SS 8. In such embodiments, instead of the display device 150 determining a pattern of proximity between the display device 150 and the SS 8 as described above, the patient's SS 8 may be configured to determine such a pattern in a variety of ways. For example, the patient's SS 8 may be configured to send a request to the display device 150 to ask the patient whether the patient is close to their display device 150 at certain points in time. The responses may be sent to the patient's SS 8 through the display device 150 and used by the patient's SS 8 to identify or learn a proximity pattern.

In certain embodiments, the patient's SS 8 may be configured to override a learned proximity pattern if the patient's SS 8 has signal loss issues, e.g., as a result of reducing transmission power based on the learned pattern. For example, the patient's SS 8 may reduce its transmission power at night based on an assumption that the patient keeps their display device 150 close to their SS 8. However, after a few nights of experiencing signal loss, the patient's SS 8 may increase its transmission power and determine that the previously learned pattern may not be reliable. In another example, the patient's SS 8 may wait for a threshold period of time (e.g., multiple days or some other amount of time) before the SS 8 attempts to reduce its transmission power again at nights. Generally, the patient's SS 8 may detect signal loss issues when it sends a message to a display device 150 and does not receive a response, while based on the protocol the SS 8 should have received a response. When signal loss is experienced, the patient's SS 8 may also immediately increase its transmission power. The SS 8 may detect the signal loss and self-increase the transmission power. The transmitter self-detection of signal loss may be accomplished based on determining that an expected message (from the display device 150) has not been detected within a threshold amount of time.

In certain embodiments, the SS 8 (at step 208) determines the proximity to the display device 150, based on sensor data/processed data. For example, the display device 150 may obtain sensor data from one or more sensors 163 of the display device 150, and may include the sensor data in one of the messages transmitted to the SS 8 in step 204. In certain embodiments, the display device 150 may process the (raw) sensor data to obtain pre-processed data, and may include the pre-processed data in one of the messages transmitted to the SS 8 in step 204.

The SS 8 may use the sensor data/processed data to determine at least one condition of the patient, and infer proximity based on the at least one condition. For example, the patient's SS 8 may determine, based on accelerometer data provided by an accelerometer (e.g., one of sensors 163), whether the patient is sleeping and infer that the SS 8 and display device 150 are in close proximity when the user is in this state. In another example, the patient's SS 8 may determine, based on accelerometer data, whether the patient is moving (e.g., walking, running, driving), and infer that the SS 8 and display device are in close proximity when the patient is moving. To increase the likelihood of making accurate predictions, this accelerometer data can be used in combination with other data, such as time of day, to infer that the SS 8 and display device 150 are in close proximity.

In certain embodiments, the display device 150 determines proximity of the display device 150 to the patient's SS 8. In FIG. 2. for example, at step 202, the display device 150 determines proximity to SS 8. In one example, the display device 150 may determine, based on accelerometer data, whether the user is sleeping and infer that the patient's SS 8 and display device 150 are in close proximity when the patient is in this state. The accelerometer data may be used in conjunction with other data (e.g., time of day, orientation sensor data, user feedback indicating whether the patient's display device is close to their SS 8 at nights, etc.) in order to infer that the patient's SS 8 and display device 150 are in close proximity. In certain embodiments, to reduce patient interaction, the display device 150 may be configured to assess whether the patient's SS 8 and display device 150 are in close proximity when the patient is not sleeping. For example, the display device 150 may be configured to infer proximity based on accelerometer data indicating that the user is moving (e.g., walking, running, driving). If the accelerometer data shows a moving speed, the display device 150 may infer that the patient has their display device 150 with them and therefore, the patient's SS 8 and display device 150 are in a certain vicinity of each other. The display device 150 can communicate the proximity determination in one of the messages transmitted to the SS 8 in step 204.

Continuing with FIG. 2, at step 210, the patient's SS 8 determines a transmission power based on proximity to the display device 150. In certain embodiments, when the determined proximity satisfies a condition (e.g., the proximity is below a threshold), the patient's SS 8 reduces transmission. Alternatively, in certain embodiments, when the determined proximity does not satisfy the condition (e.g., the proximity is greater than or equal to the threshold), the patient's SS 8 refrains from reducing transmission power. For example, the patient's SS 8 may use a default constant transmission power.

In certain embodiments, subsequent to reducing transmission power when the determined proximity satisfies the condition, the patient's SS 8 may determine a channel quality (e.g., amount of signal loss) between the patient's SS 8 and the display device 150. If the channel quality meets a certain threshold, then the patient's SS 8 continues to transmit signals with the reduced transmission power. On the other hand, if the channel quality does not meet the threshold, then the patient's SS 8 increases its transmission power.

In certain embodiments, the proximity of the patient's SS 8 to a display device 150 may be determined based on one or more other display devices. A nearby display device (e.g., a device of a friend or family member of the patient, or another device of the patient) can indicate that less power could be used. For example, the other user's display device may be closer to the patient's SS 8 than the patient's display device. In this scenario, the patient's SS 8 can transmit with reduced power to the other user's display device. The other user's display device can then forward data to a cloud (e.g., server system 134) and/or to another one of the patient's display devices. The patient's display device could then download the data from the cloud or the other patient's display device. In some examples, the nearby display device may be an Internet of Things (IOT) device (e.g., a connected TV, fridge, etc.) that is in closer proximity to the SS 8 than the patient's display device. In such a scenario, the patient's SS 8 can transmit with reduced power to the IoT device. The IoT device can then forward data to a cloud (e.g., server system 134) and/or to another one of the patient's display devices. The patient's display device could then download the data from the cloud or the IoT device.

In certain embodiments, the patient's SS 8 may identify that another secondary display device 150 is closer to the patient's SS 8 than the primary display device 150 based on RSSI. Once the patient's SS 8 is able to identify that the secondary display device 150 is more proximate, then the patient's SS 8 is able to reduce its transmission power and transmit omni-directionally, in which case the messages may reach the other secondary display device and the secondary display device can upload to the cloud.

Figure 3:
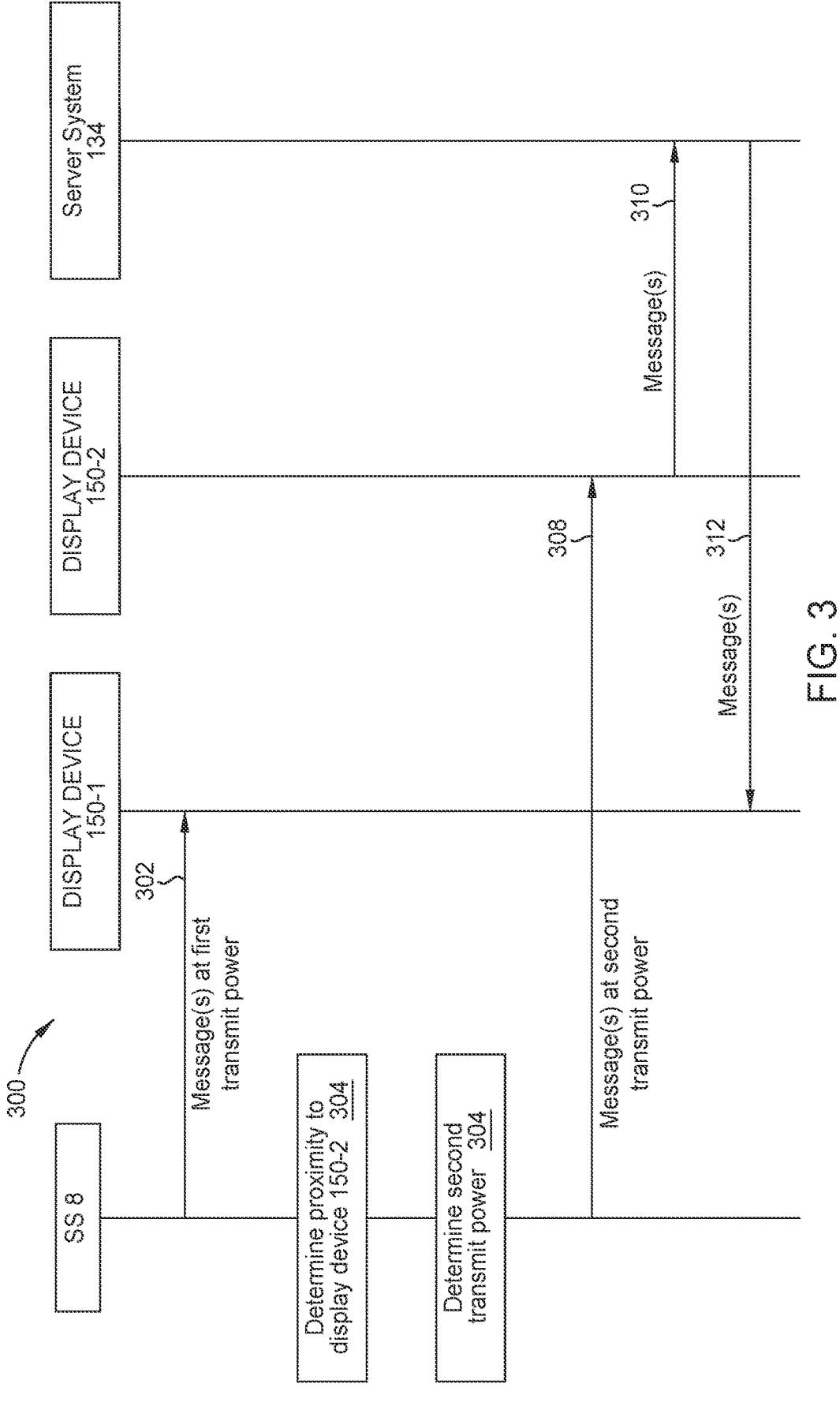
FIG. 3 is a sequence diagram illustrating example operations performed by an analyte sensor system and one or more display devices, according to certain embodiments described herein.

FIG. 3 is a sequence diagram 300 illustrating example operations performed by an SS 8, a display device 150-1, and a display device 150-2, according to certain embodiments described herein. Note that certain steps in sequence diagram 300 may occur out of the order noted in FIG. 3. For example, two steps shown in succession may, in fact, be executed substantially concurrently, or the steps may sometimes be executed in the reverse order, depending upon the functionality involved.

At step 302, the patient's SS 8 transits one or more messages using a first transmit power to a primary display device 150-1. As noted, the first transmit power may be a default constant transmission power.

At step 304, the patient's SS 8 determines that a secondary display device 150-2 is closer to the patient's SS 8 than the primary display device 150-1. As noted, the patient's SS 8 may determine that the secondary display device 150-2 is closer to the patient's SS 8 than primary display device 150-2 based on RSSI. At step 306, the patient's SS 8 determines a second transmit power. The second transmit power is lower than the first transmit power.

At step 308, the patient's SS 8 transmits one or more messages using the second transmit power to the secondary display device 150-2. In certain embodiments, the patient's SS 8 may transmit the one or more messages omni-directionally at step 308, so that the messages can reach the secondary display device 150-2.

At step 310, the secondary display device 150-2 forwards (e.g., uploads) the message(s) to the server system 134, which may be located in a cloud environment. In certain embodiments, if the patient's SS 8 uses application layer encryption or secure broadcast messaging to transmit encrypted data, the secondary display device 150-2 may use an encryption key shared with the display device 150-2 to receive the data, decrypt it, and upload it to the server system 134.

At step 312, the server system 134 transmits the message(s) to the primary display device 150-1. For example, the server system 134 may make the message(s) (including analyte data) available for download to the primary display device 150-1. As long as the primary display device 150-1 has the ability to access the location where the data is stored, the primary display device 150-1 can access the data. In certain embodiments, the primary display device 150-1 is the patient's smartphone and the secondary display device 150-2 is another user's smartphone (e.g., the patient's wife's smartphone, the patient's friend's smartphone, etc.) or another display device of the patient.

In certain embodiments, if the density of nearby display devices that can receive and/or share data with the patient's SS 8 increases (e.g., above a threshold), then the patient's SS 8 may be able to decrease its transmission power since the increased density of nearby display devices may indicate that the patient's SS 8 can transmit omni-directionally with reduced power, to allow one of the nearby display devices to receive messages from the patient's SS 8. For example, a mesh network of display devices (with BLE connectivity) can be deployed in an environment (e.g., home, hospital, etc.) to reduce signal loss between the patient's SS 8 and one or more display devices 150 within the environment as the patient's SS 8's location changes within the environment.

Accordingly, when the patient's SS 8 is deployed in an environment with a mesh network, the patient's SS 8 can infer that it will be in close proximity to at least one display device 150 while it is in the environment and can reduce its transmission power to reduce battery consumption. When one of the display devices 150 receives a message from the patient's SS 8, the display device 150 can upload the message to the cloud (e.g. server system 134), and the patient's display device 150 can subsequently download it from the cloud. In other words, it is not necessary for the patient's SS 8 to be in close proximity to the patient's primary display device 150 as long as the patient's SS 8 is in close proximity to a display device that is capable of having a shared key to decrypt the received communication. In some embodiments, the primary display device may be a car or television, and the secondary display device may be a smartwatch or smartphone.

In later Wi-Fi protocols, devices generally decrease transmission power to reduce interference. The same principle can apply here for BLE devices. For example, the traffic from all BLE devices could be reduced to reduce interference and then more BLE devices can be added throughout an environment to ensure that even with reduced transmission power, the BLE devices will always receive the communication from the patient's SS 8 and upload it to the cloud or some other central system.

In some examples, a user may deploy an IoT network of devices in a home environment to maximize battery life of the patient's SS 8. As this is deployed, special software on a user device, such as a laptop, could measure the signal strength and conductivity of specific locations throughout a home. This could be done with BLE devices by secure broadcast messaging, variable power transmission, etc. The user can then expertly place devices in the home. The special Bluetooth software in this case could configure the patient's SS 8 to only transmit so far when it is in these certain locations.

Figure 4:
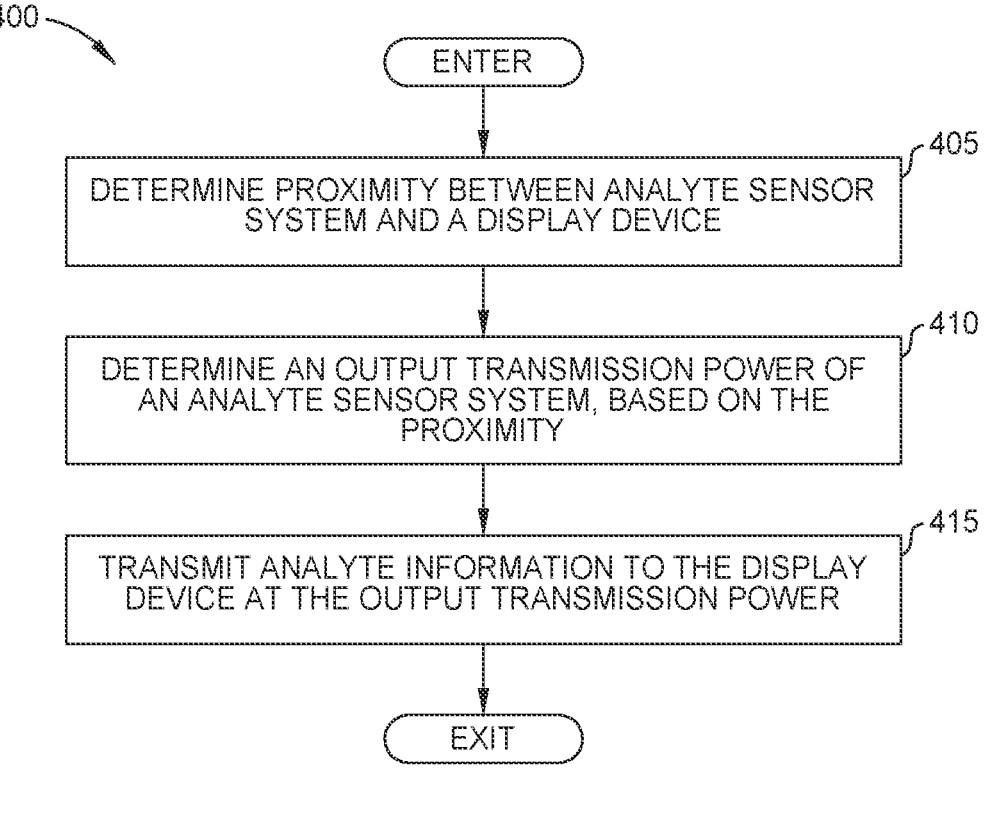
FIG. 4 is a flow diagram illustrating example operations for variable power transmission for a battery-powered device, according to certain embodiments described herein.

FIG. 4 is a flow diagram illustrating example operations 400 for variable power transmission for a battery-powered device, such as an analyte sensor system (e.g., SS 8). The operations 400 may be performed by an analyte sensor system (e.g., SS 8).

At operation 405, the analyte sensor system determines proximity between the analyte sensor system and a display device (e.g., display device 150). Operation 405 may be implemented based on any one of (or combination of) information inputs described herein.

At operation 410, the analyte sensor system determines an output transmission power of the analyte sensor system, based on the proximity. In certain embodiments, the output transmission power is a default constant transmission power. Alternatively, in certain embodiments, the output transmission power is a reduced transmission power (e.g., lower than the default constant transmission power).

At operation 415, the analyte sensor system transmits analyte information to the display device at the output transmission power.

Figure 5:
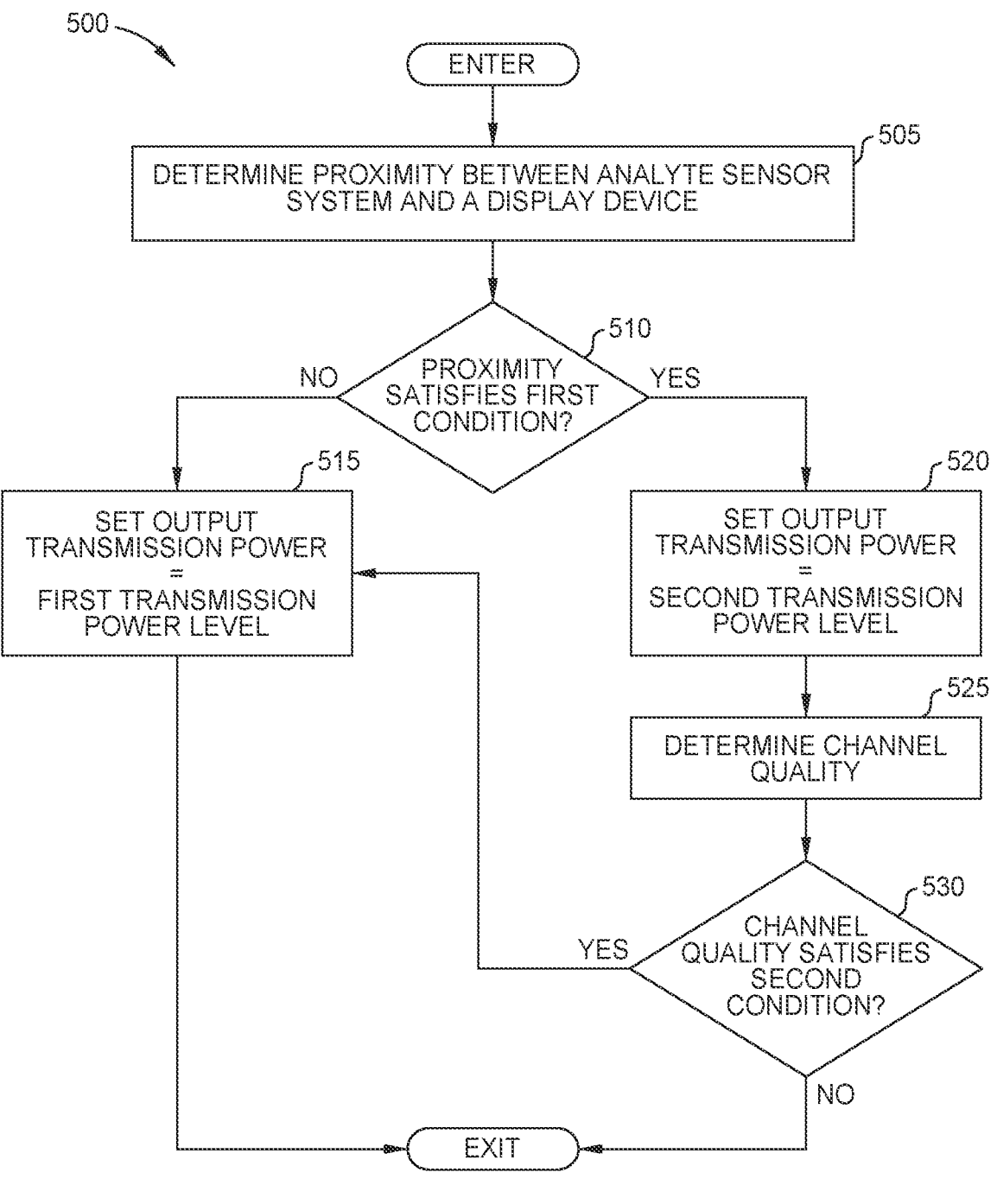
FIG. 5 is a flow diagram illustrating example operations for variable power transmission for a battery-powered device, according to certain embodiments described herein.

FIG. 5 is a flow diagram illustrating example operations 500 for variable power transmission for a battery-powered device, such as an analyte sensor system (e.g., SS 8). The operations 500 may be performed by an analyte sensor system (e.g., SS 8).

At operation 505, the analyte sensor system determines proximity between the analyte sensor system and a display device. Operation 505 may be implemented based on any one of (or combination of) information inputs described herein.

At operation 510, the analyte sensor system determines if the proximity satisfies a first condition (e.g., the proximity is less than a first threshold). If the proximity does not satisfy the first condition (e.g., the proximity is greater than or equal to the first threshold), then, at operation 515, the analyte sensor system sets the output transmission power equal to a first transmission power level. On the other hand, if the proximity satisfies the first condition, then, at operation 520, the analyte sensor system sets the output transmission power equal to a second transmission power level. The first transmission power level is greater than the second transmission power level.

At operation 525, the analyte sensor system determines a channel quality of a communication channel between the analyte sensor system and the display device. Operation 525 may be implemented using any one of the above techniques described herein. At operation 530, the analyte sensor system determines whether the channel quality satisfies a second condition (e.g., channel quality is less than a second threshold). If so, then, at operation 515, the analyte sensor system sets the output transmission power equal to the first transmission power level. That is, the analyte sensor system may increase the output transmission power from the second transmission power level to the first transmission power level. On the other hand, if the channel quality does not satisfy the second condition (e.g., channel quality is greater than or equal to the second threshold), then the analyte sensor system may keep the output transmission power at the second transmission power level.

Advantageously, by using the variable power transmission techniques described herein, battery-powered analyte sensor systems can reduce battery consumption by reducing the amount of power that the analyte sensor system uses to transmit messages over time.

As used herein, "a processor," "at least one processor," or "one or more processors" generally refers to a single processor configured to perform one or multiple operations or multiple processors configured to collectively perform one or more operations. In the case of multiple processors, performance of the one or more operations could be divided amongst different processors, though one processor may perform multiple operations, and multiple processors could collectively perform a single operation. Similarly, "a memory," "at least one memory," or "one or more memories" generally refers to a single memory configured to store data and/or instructions or multiple memories configured to collectively store data and/or instructions.

Each of these non-limiting examples can stand on its own or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A computer-implemented method for performing variable power transmission of a transmitter of an analyte sensor system, the computer-implemented method comprising:
determining a proximity of the transmitter to a first display device based on a user pattern associated with a user of the first display device;
determining an output transmission power of the transmitter based on the proximity; and
transmitting analyte information from an analyte sensor coupled to the transmitter to the first display device at the output transmission power.

2. The computer-implemented method of claim 1, wherein the user pattern indicates a proximity pattern of the transmitter to the first display device over time.

3. The computer-implemented method of claim 2, wherein determining the proximity of the transmitter comprises determining, at a first time instance, that the proximity of the transmitter to the first display device is less than a threshold, based on the proximity pattern.

4. The computer-implemented method of claim 1, further comprising receiving an indication of the user pattern from the first display device.

5. The computer-implemented method of claim 1, further comprising determining the user pattern based on information received from the first display device.

6. The computer-implemented method of claim 5, wherein the information comprises an indication of when the user of the first display device is within a threshold distance to the first display device over time.

7. The computer-implemented method of claim 5, wherein the information comprises sensor data from one or more sensors of the first display device.

8. The computer-implemented method of claim 1, wherein determining the output transmission power comprises:
setting the output transmission power to a first transmission power level when the proximity is greater than or equal to a first threshold; or
setting the output transmission power to a second transmission power level when the proximity is less than the first threshold, wherein the second transmission power level is less than the first transmission power level.

9. The computer-implemented method of claim 8, further comprising, after setting the output transmission power to the second transmission power level:
determining a quality of a channel between the transmitter and the first display device; and
determining whether to adjust the output transmission power, based on the quality of the channel.

10. The computer-implemented method of claim 9, wherein determining whether to adjust the output transmission power comprises determining to increase the output transmission power when the quality of the channel is less than a second threshold.

11. The computer-implemented method of claim 9, wherein determining whether to adjust the output transmission power comprises determining to refrain from increasing the output transmission power when the quality of the channel is greater than or equal to a second threshold.

12. The computer-implemented method of claim 1, further comprising:

determining a proximity of the transmitter to a second display device; and upon determining that the proximity of the transmitter to the second display device is less than the proximity of the transmitter to the first display device, transmitting the analyte information at the output transmission power to the second display device.

13. An analyte sensor system, comprising:

an analyte sensor; and sensor electronics coupled to the analyte sensor and comprising a processor and a transmitter, wherein:

the processor is configured to:

determine a proximity of the transmitter to a first display device based on a user pattern associated with a user of the first display device; and determine an output transmission power of the transmitter based on the proximity; and the transmitter is configured to transmit analyte information from the analyte sensor to the first display device at the output transmission power.

14. The analyte sensor system of claim 13, wherein the user pattern indicates a proximity pattern of the transmitter to the first display device over time.

15. The analyte sensor system of claim 13, wherein determining the output transmission power comprises:

setting the output transmission power to a first transmission power level when the proximity is greater than or equal to a first threshold; or setting the output transmission power to a second transmission power level when the proximity is less than the first threshold, wherein the second transmission power level is less than the first transmission power level.

16. The analyte sensor system of claim 15, wherein the processor is further configured to:

determine a quality of a channel between the transmitter and the first display device; and determine whether to adjust the output transmission power, based on the quality of the channel.

17. The analyte sensor system of claim 13, wherein:

the processor is further configured to determine a proximity of the transmitter to a second display device; and the transmitter is configured to transmit the analyte information at the output transmission power to the second display device, when the proximity of the transmitter to the second display device is less than the proximity of the transmitter to the first display device.

18. A non-transitory computer-readable medium storing computer- executable instructions, which when executed by one or more processors of a display device, performs an operation for variable power transmission of a transmitter of an analyte senor system, the operation comprising:

determining a pattern of proximity of the transmitter to a display device;

determining an output transmission power of the transmitter based on the proximity; and transmitting analyte information from an analyte sensor coupled to the transmitter to the display device at the output transmission power.

19. A display device comprising:

one or more memories collectively storing computer-executable instructions; and one or more processors coupled to the one or more memories, the one or more processors being collectively configured to execute the computer-executable instructions and cause the display device to perform an operation comprising:

determining a pattern of proximity of the display device to a transmitter of an analyte sensor system;

transmitting an indication of the pattern of proximity to the analyte sensor system; and receiving an analyte transmission from the transmitter, the analyte transmission having an output transmission power based at least in part on the indication.

20. The display device of claim 19, the operation further comprising determining a user pattern associated with a user of the display device.

21. The display device of claim 20, wherein the pattern of proximity is determined based on the user pattern.

22. The display device of claim 20, wherein the pattern of proximity comprises the user pattern.

23. The display device of claim 19, wherein the pattern of proximity is determined based on at least one of (i) sensor data from one or more sensors of the display device or (ii) user feedback.

24. A system comprising:

a display device; and an analyte sensor system comprising an analyte sensor, a processor, and a transmitter, the analyte sensor system being configured to:

determine, via the processor, a pattern of proximity of the transmitter to the display device;

determine, via the processor, an output transmission power of the transmitter based on the proximity; and transmit, via the transmitter, analyte information from the analyte sensor to the display device at the output transmission power.

25. The system of claim 24, wherein the display device is configured to:

determine a pattern of proximity of the display device to the transmitter; and transmit an indication of the pattern of proximity to the analyte sensor system.

26. The system of claim 25, wherein the proximity of the transmitter to the display device is determined based on the indication.

27. The system of claim 25, wherein the display device is configured to determine a user pattern associated with a user of the display device.

28. The system of claim 27, wherein the pattern of proximity is determined based on the user pattern.

29. The system of claim 24, wherein determining the output transmission power comprises:

setting the output transmission power to a first transmission power level when the proximity is greater than or equal to a first threshold; or setting the output transmission power to a second transmission power level when the proximity is less than the first threshold, wherein the second transmission power level is less than the first transmission power level.

* * * * *